United States Patent [19]
Yoshihara et al.

[11] Patent Number: 5,882,648
[45] Date of Patent: Mar. 16, 1999

[54] METHODS OF DISEASE INHIBITION USING ACID POLYSACCHARIDES EXTRACTED FROM NUTSHELLS

[75] Inventors: Masazumi Yoshihara, 1-12, Kawaramachi, Naka-ku, Hiroshima City, Hiroshima Pref.; Naoki Yamamoto, Ube; Masakazu Unten, Kawasaki, all of Japan

[73] Assignee: Masazumi Yoshihara, Hiroshima, Japan

[21] Appl. No.: 714,495

[22] Filed: Sep. 16, 1996

Related U.S. Application Data

[63] Continuation of Ser. No. 308,213, Sep. 19, 1994, abandoned, which is a continuation of Ser. No. 15,131, Feb. 9, 1993, abandoned, which is a continuation of Ser. No. 770,152, Oct. 3, 1991, abandoned, which is a continuation of Ser. No. 452,833, Dec. 21, 1989, abandoned.

[30] Foreign Application Priority Data

Dec. 26, 1988 [JP] Japan .................................. 63-328483

[51] Int. Cl.⁶ .................................................. A61K 35/78
[52] U.S. Cl. ............................................... 424/195.1
[58] Field of Search ........................................... 424/195.1

[56] References Cited

U.S. PATENT DOCUMENTS

| | | | |
|---|---|---|---|
| 95,209 | 9/1869 | Draper | 424/195.1 |
| 3,928,584 | 12/1975 | Hudson | 424/195.1 |
| 4,352,796 | 10/1982 | Arichi | 424/195 |
| 4,767,861 | 8/1988 | Boulware | 546/41 |
| 4,769,452 | 9/1988 | Boulware | 540/476 |
| 4,789,545 | 12/1988 | Woods | 424/101 |
| 5,141,958 | 8/1992 | Crozier-Willi | 514/558 |
| 5,241,091 | 8/1993 | Yoshihara et al. | 554/13 |

FOREIGN PATENT DOCUMENTS 2856577  6/1980  Germany .................................. 491/14

OTHER PUBLICATIONS

Remington, 3rd Ed. 1895, Practice of Pharmacy, pp. 438–439, 450–453.
Steinmetz, Codex Vegetabilis, 1957, # 606.
Mitsuya et al, "Retroviruses in Human Lymphoma Leukemia", Japan SCI SOC Press 1985, pp. 277–288.
Sandstrom et al, "Anti Viral Therapy in AIDS," AIDS Press Ltd., 1987, pp. 373–390.
Aldrich catalog 1992, Aldrich Chemical Co Milwaukee WI, pp. 89, 1049, 1119.
Bhargava U., Antitumor Activity of Juglans . . . J of Pharm Sciences vol. 57 No.10 Oct. 1968. pp. 1674–1677.
Bhargava U., Antitumor Activity of Juglans . . . J of Pharmaceutical Sciences 57 vol. 1968 pp. 1674–1677.

*Primary Examiner*—Ralph Gitomer
*Attorney, Agent, or Firm*—Pillsbury Madison & Sutro Intellectual Property Group

[57] ABSTRACT

An anti-AIDS viral agent and anticancer agent comprising as an effective ingredient in the extract containing polysaccharides from nutshells of nuts belonging to the genus Juglans or the genus Carya of angiosperm Juglandaceae with an alkali aqueous solution is disclosed. The extract has anti-HIV effect at the concentration ranging from 64 to 512 $\mu$g/ml and exhibits an increased life span in animal.

2 Claims, 3 Drawing Sheets

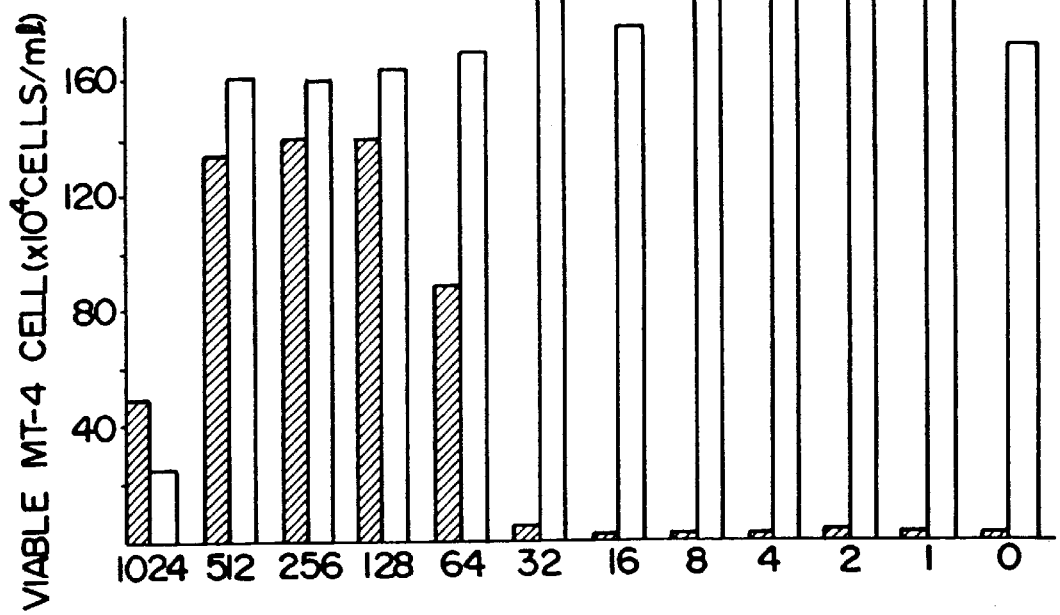
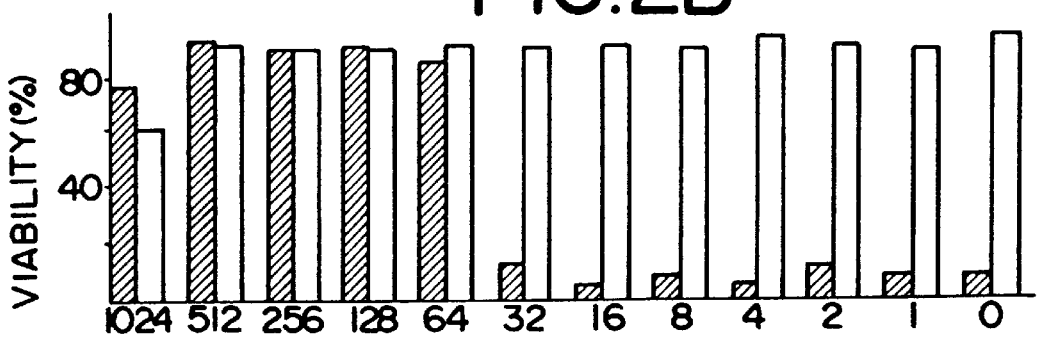
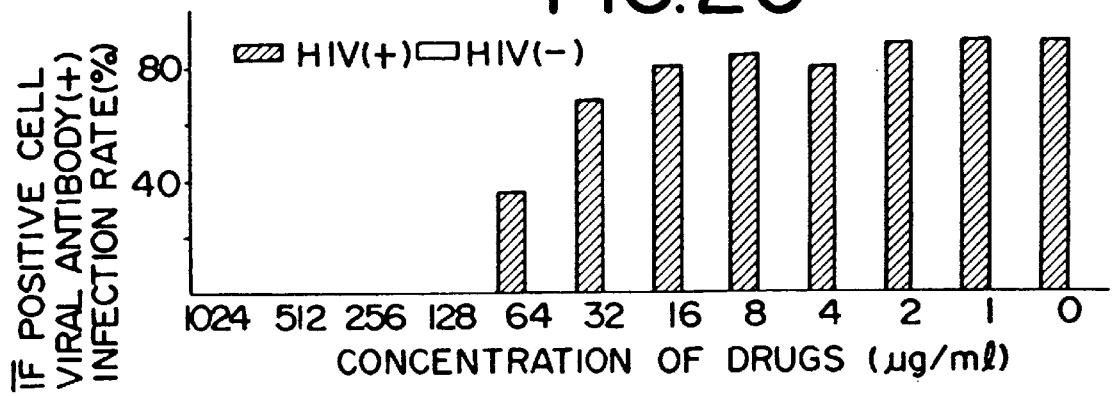

METHODS OF DISEASE INHIBITION USING ACID POLYSACCHARIDES EXTRACTED FROM NUTSHELLS

This is a continuation of application Ser. No. 08/308,213, filed on Sep. 19, 1994, abandoned upon the filing hereof, which is a continuation of 08/015,131 filed Feb. 9, 1993 now abandoned which is a continuation of 07/770,152 filed Oct. 3, 1991 now abandoned, which is a cont. of 07/452,833 filed Dec. 21, 1989 now abandoned.

BACKGROUND OF THE INVENTION

1. Field of the Invention

The present invention relates to an anti-AIDS viral agent and anticancer agent comprising polysaccharides which are extracted from nuts, mainly nutshells of deciduous tall trees belonging to the genus Juglans or the genus Cayra of angiosperm Juglandaceae.

2. Description of the Prior Art

At present, various compounds have been proposed as anti-AIDS viral agents and anticancer agents and developed as drugs. However, it is the actual situation that any decisive drug has not yet been obtained in view of effects, side effects, etc.

The present inventors found that substances having an extremely high physiological activity were contained in the extract from nutshells of a pine.

It was positively confirmed by in vitro tests and the like that in particular, polysaccharides contained in the extract could activate granulocytes in leucocytes contained in blood and were protective against infectious diseases with E. coli and various viruses including herpes virus and against cancer.

Therefore, the present inventors have further attempted to extract the effective compound from various natural nutshells. As a result, it has been revealed that polysaccharides similar to the substances extracted from the pine nutshells described above are also contained in the extract from shells of nuts belonging to the genus Juglans or the genus Carya of angiosperm Juglandaceae. It has then been confirmed that the polysaccharides have inhibitory effect to viral infections, that is, an effect of preventing proliferation or virus and further have a carcinostatic activity against cancer.

SUMMARY OF THE INVENTION

The present invention aims at providing an anti-AIDS viral agent and anticancer agent comprising polysaccharides as an effective ingredient extracted from nutshells of nuts belonging to the genus Juglans or the genus Carya of angiosperm Juglandaceae.

BRIEF DESCRIPTION OF THE DRAWINGS

FIGS. 2(a)–(c) are graphs showing the results on the cell growth prevention effect and the cytotoxicity of the extract according to the present invention as an anti-AIDS viral agent.

DETAILED DESCRIPTION OF PREFERRED EMBODIMENTS

Figure 1A:
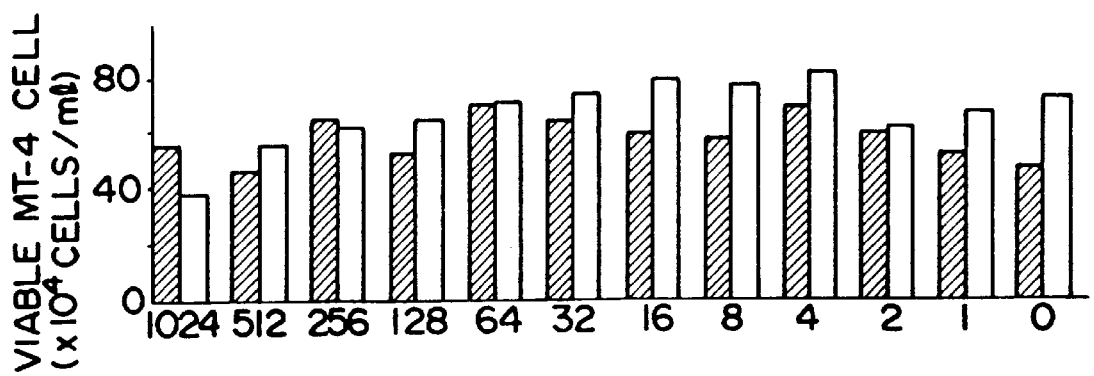
FIGS. 1(a)–(c) are graphs showing the results on the cell growth prevention effect and the cytotoxicity of the extract according to the present invention as an anti-AIDS viral agent.

As a means for attaining the object described above, nutshells (dry shells) belonging to the genus Juglans or the genus Carya of angiosperm Juglandaceae are finely ground with a grinder, etc. Then, the ground shells are immersed in an alkali aqueous solution and extracted with an alkali water.

Next, an appropriate acid such as acetic acid, etc. is added to the extracted liquid to neutralize. Thereafter, salts are removed by dialysis, membrane separation, etc. and at the same time, the mixture is centrifuged by a centrifuging machine, etc. and the extracted substances are precipitated. The precipitates are filtered and the filtrate is concentrated. The resulting solid is freeze dried to recover the powdery extract.

Example of extraction treatment:

In the example, shells of nuts belonging to the genus Carya were ground with a grinder and 10 l of 0.85% ammonia water was added to 1 kg of the ground shells. The mixture was stirred at 40° C. for 5 hours.

Next, the liquid was filtered and acetic acid was added to he filtrate (9.5 l) to neutralize to pH of 6.5. After dialyzing through a dialysis membrane, the recovered substance was freeze dried. As the result, the powdery extract showing light brown color could be obtained. The yield was 40 g based on 1 kg of the ground shells.

1. Anti-AIDS viral test with the extract

Using MT-4 cell, a HTLV-I carrying cell line, anti-HIV tests (proliferation of cells or viable cells, viability rate of cells, HIV antigen positive rate by IF) of the extract described above in the cell free viral infection system and cytotoxicity test of HIV-uninfected MT-4 cells described above were performed as described below.

Notes: HIV . . . AIDS virus

IF . . . immunofluorescence (1) Cells used for the tests

Cells for the test were produced as follows. MT-4 cells were cultured in RPMI-1640 (RPMI stands for Rosewell Park Memorial Institute) medium plus 10% fetal calf serum. After the cell density was adjusted to $60 \times 10^4$ counts/ml, the cells were centrifuged and a fresh medium was added thereto to divide into two equal portions. One was provided for the viral infection test and another was provided for the cytotoxicity test.

(2) Virus used in the tests

HIV (human immunodeficiency viruses) having a cell density of $3.4 \times 10^5$ PFU/ml (3) Method (a) Method for virus infection The cells for the tests prepared in (1) described above were infected with HIV sample of (2) in m.o.i=0.002. After maintaining at 37° C. for an hour to adsorb, centrifugation was again performed. RPMI-1640 medium plus 10% fetal calf serum (culture medium) was added to adjust the respective cell densities of the infected cells and the intact cells to $60 \times 10^4$ (finally $30 \times 10^4$) counts/ml, respectively.

(b) Distribution of cells

Into each well of a 24-well microplate, 0.5 ml of the infected and unifected cells prepared as in (a) were charged.

(c) Dilution and addition of the extract (drug)

The extract solution (drug) of the present invention obtained by dissolving the extract in PBS (phosphate buffered saline) in a concentration of 5 mg/ml was sterilized by filtering through a filter having a pore size of 0.22 μm. However, the extract was not fully dissolved but some residue actually remained. Thus, filtration was performed in order using filters having pore sizes of 0.8, 0.45 and 0.22 μm sequentially. The respective solutions collected from the thus filtered extract solutions (drug) were adjusted with RPMI-1640 medium to show concentrations within parentheses.

2048 (1020 after the adjustment), 1024 (512), 512 (256), 256 (128), 128 (64), 64 (32), 32 (16), 16 (8), 8 (4), 4 (2), 2 (1), 0 (test standard)

From these solutions having these concentrations, 0.5 ml each was taken and added to the 24 wells of microplate, in which the cells had been distributed and the infected and uninfected MT-4 cells had already been charged by the method in (a), to make the minimum cell density $30 \times 10^4$/ml.

2. Test on HIV-induced cytotoxicity and on cytotoxicity induced by the extract of the present invention Vital cells were counted and the viability rate was visually observed on Day 3 and Day 6. Furthermore a test to find HIV-specific antigen was performed on Day 3 and Day 6, using indirect immunofluorescence.

The results are shown in Tables 1 and 2 below.

TABLE 1

| Concentration | Extract (Drug) | | | |
| --- | --- | --- | --- | --- |
| | HIV (+) | | HIV (−) | |
| of Drug | Day 3 | Day 6 | Day 3 | Day 6 |
| 1024 cell n | 9 + 56 | 14 + 52 | 6 + 39 | 15 + 26 |
| % viab. | 86 | 79 | 87 | 63 |
| % IF p. | <0.2 | <0.2 | <0.2 | <0.2 |
| 512 cell n | 6 + 47 | 8 + 140 | 5 + 56 | 12 + 167 |
| % viab. | 89 | 95 | 92 | 93 |
| % IF p. | <0.2 | <0.2 | <0.2 | <0.2 |
| 256 cell n | 5 + 65 | 13 + 146 | 5 + 62 | 15 + 167 |
| % viab. | 93 | 92 | 93 | 92 |
| % IF p. | <0.2 | <0.2 | <0.2 | <0.2 |
| 128 cell n | 6 + 53 | 11 + 146 | 3 + 65 | 15 + 170 |
| % viab. | 90 | 93 | 90 | 92 |
| % IF p. | <0.2 | <0.2 | <0.2 | <0.2 |
| 64 cell n | 7 + 70 | 13 + 93 | 5 + 71 | 14 + 177 |
| % viab. | 91 | 88 | 93 | 93 |
| % IF p. | <0.2 | 37 | <0.2 | <0.2 |
| 32 cell n | 7 + 65 | 40 + 6 | 4 + 75 | 18 + 205 |
| % viab. | 90 | 13 | 95 | 92 |
| % IF p. | 1.7 | 71 | <0.2 | <0.2 |

TABLE 2

| Concentration | Extract (Drug) | | | |
| --- | --- | --- | --- | --- |
| | HIV (+) | | HIV (−) | |
| of Drug | Day 3 | Day 6 | Day 3 | Day 6 |
| 1024 cell n | 3 + 60 | 36 + 2 | 7 + 80 | 13 + 185 |
| % viab. | 94 | 5.3 | 92 | 93 |
| % IF p. | 3.12 | 8.3 | <0.2 | <0.2 |
| 512 cell n | 5 + 58 | 31 + 3 | 4 + 78 | 19 + 208 |
| % viab. | 92 | 8.8 | 95 | 92 |
| % IF p. | 4.5 | 8.72 | <0.2 | <0.2 |
| 256 cell n | 6 + 69 | 32 + 2 | 5 + 81 | 10 + 219 |
| % viab. | 92 | 5.9 | 94 | 96 |
| % IF p. | 7.7 | 82 | <0.2 | <0.2 |
| 128 cell n | 5 + 60 | 30 + 4 | 4 + 62 | 16 + 205 |
| % viab. | 92 | 12 | 94 | 93 |
| % IF p. | 9.6 | 91 | <0.2 | <0.2 |
| 64 cell n | 4 + 52 | 21 + 2 | 6 + 67 | 17 + 198 |
| % viab. | 93 | 8.7 | 92 | 92 |
| % IF p. | 11.5 | 92 | <0.2 | <0.2 |
| 32 cell n | 10 + 47 | 29 + 3 | 4 + 72 | 6 + 178 |
| % viab. | 82 | 9.4 | 95 | 97 |
| % IF p. | 12.9 | 91 | <0.2 | <0.2 |

Notes: cell n . . . The number of cells counted; when it is shown by 4+60, this indicates 4 dead cells and 60 vital cells.

(3) Results of test of HIV

Figure 1B:
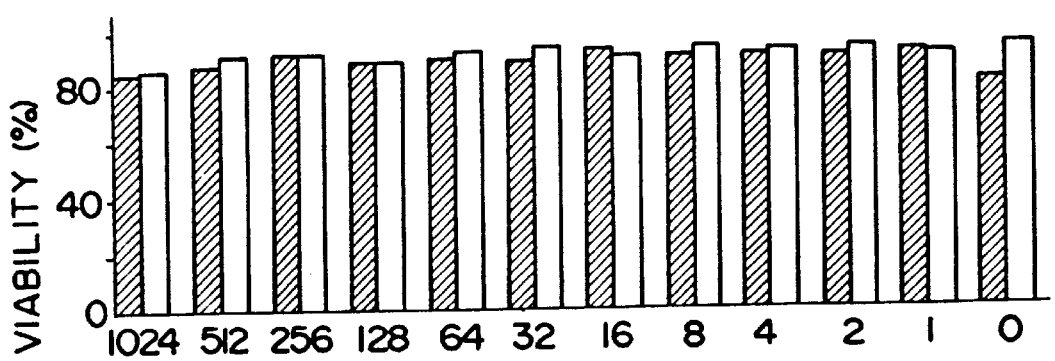
Figure 1C:
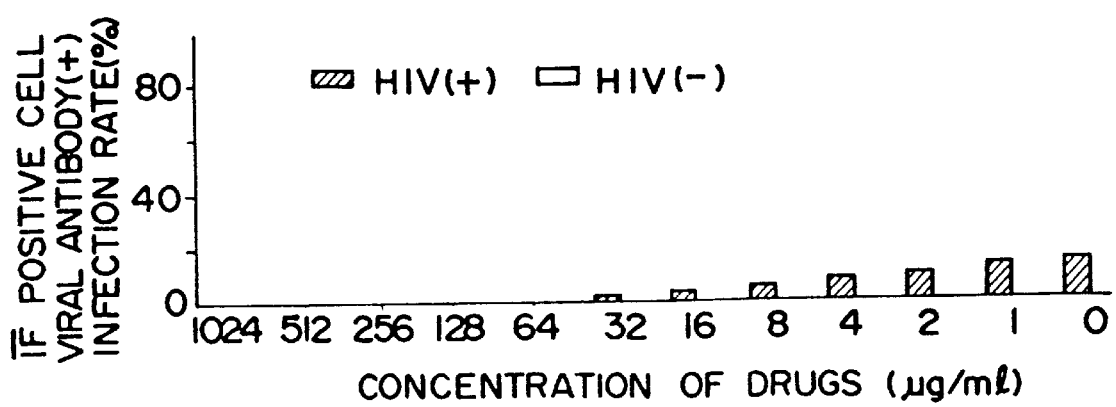

Cell proliferation in the group added with the extract (drug) of the present invention (1 to 256 μg/ml) was almost equal to that in the intact group without drug (cf. FIG. 1 A).

From the results, it is believed that the cytotoxicity of the extract (drug) of the present invention would be extremely low. On Day 6 after the incubation, HIV-infected cells without drug were almost killed but most cells were alive (60 to 90% of the non-infected cells were alive) in the group added with the extract (drug) of the present invention (64 to 512 μg/ml) (cf. FIGS. 2 A and B). Furthermore, on Day 6 after the incubation, the frequency of HIV antigen-positive cells was 90% in the drug-free control group but in the group added with the extract (drug) of the present invention (128 μg/ml or more), the viral antigen-positive cells were almost negative (0.2% or less) (cf. FIG. 2 C). From the foregoing experimental results, it has been proven that the use of the extract according to the present invention as a drug in a concentration of 64 to 512 μg/ml after diluting with PBS showed anti-HIV effect.

2. Test for carcinostatic activity

Next, the powdery extract obtained by the example was examined as described below, with respect to its carcinostatic activity as a drug.

(a) Preparation of cancer-bearing mice

Sarcoma 180 cells were intraperitoneally administered to ICR (Institute of Cancer Research) mice of 5 week age weighing about 25 g in a dose of $1 \times 10^6$ to prepare cancer-bearing mice.

(b) Preparation of injection from the extract

In 5 ml of physiological saline 5 mg of the powdery extract was dissolved. The solution was filtered through a millipore filter for sterilization to make injection A. Injection A was diluted to 10-fold with physiological saline to make injection B.

(c) Method for evaluation of carcinostatic effect

Injection A or B described above and physiological saline as a control were intraperitoneally administered to the cancer-bearing mice prepared in (a) above, respectively, in a dose of 0.2 ml. The number of days the mice survived and the number of the alive mice were counted.

(d) Results of the carcinostatic activity

Figure 3:
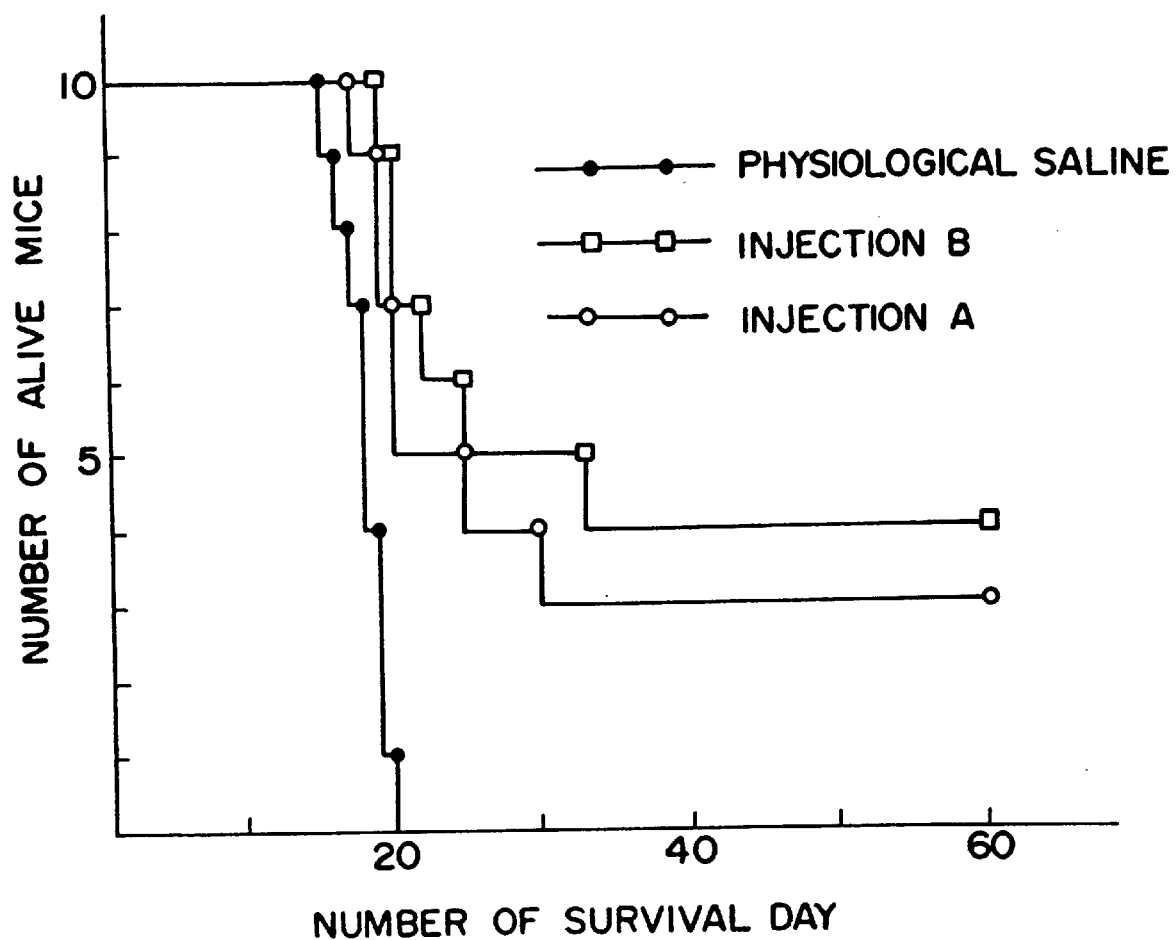
FIG. 3 shows the results obtained by the test on carcinostatic activity.

The number of the alive mice and the number of days the mice survived are taken on the ordinate and on the abscissa, respectively. The results are shown in FIG. 3.

From the figure, the total number of the survival days is counted as follows, respectively, in the group administered with physiological saline, the group administered with injection A and the group administered with injection B.

Group administered with physiological saline=(1×15)+(1×16)+(1×17)+(3×18)+(3×19)+(1×120)=179

Group administered with injection A=(1×17)+(2×19)+(2×20)+(1×25)+(1×30)+(3×60)=330

Group administered with injection B=(1×19)+(2×20)+(1×22)+(1×25)+(1×33)+(4×66)=379

As described above, the survival day number was 17.9 days in the group administrated with physiological saline, 33.0 days in the group administrated with injection A and 37.9 days in the group administrated with injection B. The results reveal that the extract (drug) according to the present invention exhibits an effective carcinostatic activity.

While the invention has been described in detail and with reference to specific embodiments thereof, it is apparent to one skilled in the art that various changes and modifications can be made therein without departing from the spirit and the scope of the invention.

What is claimed is:

1. A method of inhibiting HIV activity in MT-4 cells infected with HIV, comprising the steps of:
    (i) culturing MT-4 cells in RPMI-1640 medium plus 10% fetal calf serum, (ii) adjusting the cell density of the MT-4 cells to $60\times10^4$ counts/ml, (iii) centrifuging the MT-4 cells, and (iv) adding fresh medium which comprises a sufficient amount of an extract highly concentrated with acid polysaccharides extracted with alkali solution from nutshells of nuts belonging to the genus Juglans or the genus Carya of angiosperm Juglandacea, so that the HIV activity in the MT-4 cells is inhibited thereby.

2. The method of claim 1, wherein said extract is extracted by the method comprising the steps of:

(i) forming an extract by extracting acid polysaccharides from ground shells of nuts belonging to the genus Juglans or the genus Carya of angiosperm Juglandacea, in an alkali aqueous solution at a temperature over 40° C.;

(ii) adding to the extract sufficient acid to neutralize the pH of the extract; and (iii) removing solids from the extract so as to form an extract highly concentrated with acid polysaccharides.

* * * * *